US005753765A

United States Patent [19]

Thomsen

[11] Patent Number: 5,753,765
[45] Date of Patent: May 19, 1998

[54] POLYMERIZABLE OLIGO- AND/OR POLYALKENOIC ACIDS

[75] Inventor: Sven Arne Thomsen, Wedel, Germany

[73] Assignee: Ernst Mühlbauer KG, Germany

[21] Appl. No.: 809,034

[22] PCT Filed: Sep. 6, 1995

[86] PCT No.: PCT/DE95/01218

§ 371 Date: Mar. 21, 1997

§ 102(e) Date: Mar. 21, 1997

[87] PCT Pub. No.: WO96/09332

PCT Pub. Date: Mar. 28, 1996

[30] Foreign Application Priority Data

Sep. 23, 1994 [DE] Germany .............. 44 33 987.9

[51] Int. Cl.$^6$ ............................................. C08F 297/02
[52] U.S. Cl. ..................... 525/288; 525/299; 525/309; 525/311
[58] Field of Search .............................. 525/288, 299, 525/309, 311

[56] References Cited

U.S. PATENT DOCUMENTS

| 5,219,945 | 6/1993 | Dicker et al. | 525/276 |
| 5,264,527 | 11/1993 | Varshney et al. | 525/299 |
| 5,314,961 | 5/1994 | Anton et al. | 525/280 |
| 5,371,147 | 12/1994 | Spinelli et al. | 525/288 |
| 5,399,620 | 3/1995 | Niessner et al. | 525/71 |
| 5,540,989 | 7/1996 | Maul et al. | 428/349 |
| 5,643,996 | 7/1997 | Rudolph et al. | 524/561 |

FOREIGN PATENT DOCUMENTS 0432727  5/1990  European Pat. Off. .

Primary Examiner—Irina S. Zemel
Attorney, Agent, or Firm—David L. Mossman

[57] ABSTRACT

Polymerizable oligo- and/or polyalkenoic acids are disclosed which are block polymers of different polyalkenoic acids or their derivatives and/or conjugated dienes. These oligo-/polyalkenoic acids are characterized in that they have at least one sequence with acid functions or protected acid functions in the side group and at least one sequence with olefinic double bonds in the side group of the alcohol component of the esters or the amine component of the amides. The use of said polymerizable oligo- and/or polyalkenoic acids for dental/medical purposes is also described.

23 Claims, No Drawings

POLYMERIZABLE OLIGO- AND/OR POLYALKENOIC ACIDS

In recent years, a large number of new and optimized bio-materials for synthetic dental/medical restorative use have been developed. The improvements were initiated by the need for materials which are very similar to the natural tooth substance with regard to esthetic-cosmetic criteria and, nevertheless, are unobjectionable from the medical point of view. Therefore, as a result of the intrinsic color of amalgam, substitution of this commonly used material for dental cements began very early whenever front teeth had to be restored.

Conventional dental cements usually consist of finely ground metal oxides, metal hydroxides, or other ion-leachable materials, e. g. glasses, plus an aqueous acid. The best known cements of this type are phosphate cement (zinc oxide+phosphoric acid) and silicate cement (powdered glass+phosphoric acid). Said cements are strictly inorganic materials, have poor adhesion to the tooth substance, and are relatively brittle. For these reasons and due to their strongly irritating effect to dental pulp, said materials have almost completely disappeared from the market.

From the discovery of polyacrylic acid, i. e. from the middle of this century, modified organic or semi-organic cements have gained increasing importance. Said materials consist of a metal oxide or metal hydroxide and a relatively high-molecular organic acid component. Among these materials, particularly carboxylate cements (zinc oxide+ polyacrylic acid) are of interest. They are used as root fillers or pulp-capping materials. Owing to their high pH-value, said materials act as barriers protecting against acids and other toxic substances that may be included in several fillers. However, the main disadvantages associated with these cements are that they set very slowly, that their mechanical strength is poor, and that said materials may be leached by aqueous media.

As a result of the serious shortcomings, dental cements have largely been replaced by more durable, insoluble composites that withstand higher stress and have higher edge strength. Said composites mainly consist of a polymerizable binder reinforced with an organic or inorganic filler. Suitable polymerizable binders are especially those compounds comprising olefinically unsaturated groups, preferably (meth)acrylic acid esters of mono- and polyhydric alcohols. Suitable inorganic fillers are finely powdered quartz, micronized silicic acids, alumina, barium glasses, or other mineral particles covered with polymerizable silane to improve their adhesion. An essential feature of composites is that they cure through free-radical polymerization of the olefinic double bonds and that no water is required to achieve curing. Besides amalgams, composites are mainly used today for dental restorative purposes, but said materials, too, have limited applications because they may cause tissue irritation and intoxication in case of deep tooth cavities, undergo polymerization shrinkage, and have insufficient adhesion to the tooth.

In the late sixties, the discovery of glass ionomer cements, more precisely termed glass polyalkenoate cements, represented a major breakthrough in dental research. Said glass polyalkenoate cements, too, are mixtures of organic components, e. g. polyalkenoic acids or hydroxycarboxylic acids, and inorganic components, such as aluminum silicate glasses or quartzes. The reaction medium required for the cement reaction is water. The reaction is the same as with other cements, namely an acid-base reaction, herein the polycarboxylic acid acts as a proton donor, while the aluminosilicate glass is the proton acceptor.

This reaction may be divided into three steps, the boundaries between the steps being fluid:
1. Hydrolysis (to be more precise: dissociation) of the acid groups and displacement of cations (first $Ca^{2+}$, then $Al^{3+}$) out of the glass.
2. Reaction of carboxylate groups with cations yielding a salt, thereby causing gelation and/or precipitation of the salt.
3. Slow formation of cation bridges cross-linking the polycarboxylic acid and improving the mechanical properties. The cement becomes insoluble.

In 1971, glass polyalkenoate cements were described in literature (Wilson, A. D., *J. Appl. Chem. Biotechnol.*, 21 (1971), p. 313) and, from that time, have been used in dentistry as filling and rebasing materials and adhesive cements. These cements have significant advantages over conventional cements and composites: they are biocompatible and have improved interoral performance, good adhesion to the tooth, and good appearance. i. e. opacity.

During the past 20 years since the invention of said materials great efforts have been made to further improve their good properties and to find new applications. For example, there were used glasses which give off fluoride ions to the adjacent tooth material, or there were admixed radiopaquing agents to facilitate radiographic detection. However, said glass polyalkenoate cements, too, did not meet all expectations. They were found to be particularly sensitive to moisture in the early stage of curing.

This problem was solved by polymerizable glass polyalkenoate cements which constitute a very interesting, new class of materials combining the advantages of composites (high mechanical strength, insolubility) with those of glass polyalkenoate cements (good adhesion to the tooth, fluoride ion release). Polymerizable glass polyalkenoate cements consist of ion-leachable aluminosilicate powder plus an acid constituent which is now polymerizable. Most of said polymerizable acids are hydrophilic, unsaturated carboxylic—or phosphoric acid compounds, such as oligomeric homo- or copolymerizates of (meth)acrylic acid and/ or the derivatives thereof. After mixing, they act as a link between aqueous glass ionomer matrix and hydrophobic plastic matrix.

But the use of polymerizable acids is not limited to polymerizable glass ionomer cements. They have equally favorable effects in dental adhesion promoters, termed bonds, and surface-modifying preparations, termed preps or conditioners. A survey of the large number of polymerizable acids and their derivatives is given in EP-B1 0 219 058 assigned to Ernst Mühlbauer KG. The compounds employed so far can be divided into two main groups:

1. Short-chain compounds, e. g. modified vinyl monomers (cf. DE-A1 41 41 174) or low-molecular (meth)acrylic acid derivatives, such as N-tolylglycine-N-glycerol methacrylate or pyromellitic acid dimethacrylate (PMDM) (cf. EP-A2 0 391 619). 4-(2-Methacryloyloxyethyl)trimellitic anhydride (4-META) (cf. EP-A1 0 425 200), dipentaerythritol-pentaacrylate-phosphoric acid ester (PENTA) (cf. EP-A1 0 554 890), or the so-called TCB resin, a butane tetracarboxylic acid-bis-HEMA ester (HEMA means hydroxyethyl methacrylate) (cf. EP-A2 0 499 180) belong to this group.
2. Long-chain compounds, e. g. unsaturated polycarboxylic acids. Preferably, copolymerizates of acrylic and maleic acid or glycidyl-polymethacrylate adducts are used (cf. EP-A2 0 329 268).

However, the disadvantage associated with these two classes of unsaturated compounds is that the final strength of the cement is still lower than that of composites. It is thus obvious that, to this point in time, no ideal or perfect dental cement has been provided.

It was the object of this invention to prepare new, polymerizable acids having a defined structure which may be adjusted according to the needs. To this end, a reproducible and universal synthesis route was to be developed.

According to this invention, the problem was solved by providing a new class of block polymers of oligo- and/or polyalkenoic acids of the general formula

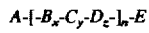

wherein the groups A and E, being the same or different, used as terminal groups are hydrogen, halogen atoms, methacrylate-, acrylate-, allyl-, vinyl-, alkyl-, aryl-, alkoxy-, aryloxy-, carboxyl-, amine-, hydroxy-, isocyanate-, silyl, and/or siloxy groups.

The oligomer/polymer consists of at least two blocks (termed herein groups) of sequences, wherein one of said groups, group B, is a segment consisting of sequences of mono-, di-, and/or tricarboxylic acids as monomeric units, the anhydrides, salts, and/or derivatives thereof having an acid protective group known as such, from which the acid can be readily set free, while the other group, group C, consists of sequences of mono-, di-, and/or tricarboxylic acid esters and/or the amides thereof as well as isoprene and/or butadiene as monomeric units, the alcohol component of the esters and the amine component of the amides each being unsaturated.

A third optional group, group D, consists of sequences of mono-, di-, and/or tricarboxylic acids as monomeric units, their esters, amides, and/or nitriles not containing any double bonds.

The order of groups B, C, and D within these blocks $[-B_x-C_y-D_z-]$ is optional and can be different for each n.

The monomeric units contained as sequences in these groups B, C, and D are the same for a certain n, but can be different for different n.

The index n represents 1 to 10 and the indices x, y, and z are 0 or 4 to 1,000, wherein for at least one n x is at least 4 and y is at least 4 and x, y, and z can be different for each n. Preferably, n is equal to 1 to 4, x and y are at least 4, and z is equal to 0 or at least 4.

According to an embodiment of this invention, the groups A, B, and C include crotonic acid, iso-crotonic acid, fumaric acid, mesaconic acid, 3-butene-1,2,3-tricarboxylic acid and, preferably, acrylic acid, methacrylic acid, maleic acid, and/ or itaconic acid as monomeric unit forming the oligomer/ polymer chain. Only for group C, the monomeric unit forming the oligomer/polymer chain may also be selected from the group of conjugated dienes, such as butadiene or isoprene.

The oligo-/polyalkenoic acids of these groups B, C, and D are different with regard to their derivation or the functionalities of their residues.

The acid of group B can be an acid, acid anhydride, the salt of said acid, or an acid having a protective group, this acid protective group being preferably a trialkylsilyl ester or a siloxy ester, most preferably trimethylsilyl.

In group B, the alcohol component of the ester or the amine component of the amide is an unsaturated alkyl residue, preferably vinyl, allyl, and/or vinylidene if the monomeric unit is an acid.

In group C, the alcohol component of the ester or the amine component of the amide is a saturated alkyl residue, preferably methyl, ethyl, propyl, tert-butyl, and/or a substituted or unsubstituted aryl residue.

According to a particularly preferred embodiment of this invention, group C is a segment consisting of oligomeric/ polymeric sequences of methacrylic acid allyl ester or—vinyl ester, while group B is a segment consisting of oligomeric/polymeric sequences of methacrylic acid trimethylsilyl ester.

Said polymerizable oligo-/polyalkenoic acids are used for dental and medical purposes, particularly as components in glass ionomer cements. These polymerizable glass polyalkenoate cements consist of ion-leachable aluminosilicate powder. After mixing and potential cross-linking of the olefinic side groups, the acid acts as a link between the aqueous glass ionomer matrix and the hydrophobic plastic matrix.

The use of said polymerizable acids is not limited to polymerizable glass ionomer cements. They show the same good properties when used in dental adhesion promoters (termed bonds), and surface-modifying preparations (termed preps or conditioners).

Furthermore, it is a novelty to prepare said polymerizable acids or their precursors by anionic polymerization yielding 'living polymers' and to form and use block polymers. It is desired that the individual blocks having adequate lengths exhibit the same behavior as the pure substance. Owing to this block structure, the carboxyl groups which are essential for reaction of the cement are in proximity to the allyl groups which are essential for radical cross-linking, thus avoiding in a favorable way steric hindrance or diffusion hindrance of the difficultly movable chain segments which would otherwise impede conversion. This is particularly important whenever highly viscous or solid polymers are used for reaction of the cement or for radical cross-linking.

This is the only procedure allowing to synthesize polymerizable acids having the structure shown hereinabove and to form blocks of the desired type and length and, furthermore, to insert the terminal groups described hereinabove.

The advantage offered by the polymerizable oligo-/ polyalkenoic acids according to this invention is that by selecting the lengths and sequences of the blocks it is possible at the synthesis stage already to predetermine the optimal number of acid functions required for reaction of the cement and of olefinic side groups cross-linkable by free-radical polymerization. Curing, final hardness, and esthetic-cosmetic criteria of the product, e. g. opacity, can be varied and optimized within a wide range.

It is favorable to perform the anionic polymerization at low temperatures because it is thus possible to selectively polymerize (meth)acrylic groups in the presence of allyl groups. The allylic double bond remains unaffected and is thus available for the ensuing radical cross-linking reaction of the polymeric segments.

Free-radical polymerization of the monomers causing polymerization of (meth)acrylic and allyl groups would result in cross-linking and insolubility of the products, thus rendering further curing of the tooth cement by radical cross-linking impossible.

Suitable solvents for use in this anionic polymerization are:

a) aliphatic and/or aromatic hydrocarbons, such as toluene, benzene, alkanes, or cycloalkanes, b) open-chain or cyclic ethers, such as tetrahydrofuran (THF), dioxane, or diethyl ether, c) ketones, heterocycles (NMP), or liquid ammonia.

Examples of suitable starter systems for said anionic polymerization are:

a) organometallic compounds, such as primary-, secondary-, tertiary butyl lithium, naphthalene-, bi-phenyl-, phenanthrene-, or anthracene complexes of the alkali metals Li, K, Na, Grignard reagents, as well as Ziegler catalysts, or potassium amide, and b) alkali metals alone.

It is essential that the monomers and solvents selected for this anionic polymerization be absolutely dry and free from chain-terminating impurities. This is expediently achieved by stirring the monomers for one day over $CaH_2$, followed by vacuum distillation in a column under nitrogen. If this treatment does not produce the desired result, the compounds concerned must be redistilled over dialkyl magnesium or stabilized Grignard reagents. Mole sieves are used for the storage of the product.

EXAMPLES

General Method of Preparation

Prior to polymerization, the reactor is baked and charged with anhydrous nitrogen. After cooling to room temperature, the solvent is charged under nitrogen, followed by chilling to −70° to −80° C. Then, the calculated amount of initiator is added and the reactor contents are allowed to cool. All of the monomer or monomers mixture to be polymerized is then charged to this mixture while stirring. The color of the solution fades, while the viscosity increases slowly. After 30 to 60 minutes, additional moieties of monomer or monomers mixture can be added. After another period of 30 to 60 minutes, the reaction is discontinued by addition of some ethanol.

Purification depends on the solvents and monomers used and is different in each experiment.

Example 1

To 40 ml of tetrahydrofuran chilled to −70° to −80° C., there was added 1 ml of a 1M solution of naphthalene sodium in THF (1 mmol). A dark-green solution was obtained to which 10 ml (9.38 g/74.4 mmol) of allyl methacrylate were quickly added. The mixture was stirred for 30 minutes. The color of the solution changed to light-yellow. Then, 5 ml (4.45 g/28.1 mmol) of methacrylic acid trimethylsilyl ester were added and stirring was continued for 30 minutes. The reaction was discontinued by adding 2 ml of ethanol. The trimethylsilyl groups were removed by stirring overnight with 5 ml of 10% aqueous HCl solution. The polymer was precipitated, then washed and dried in vacuo. The molecular weight range determined by GPC was 35,000–40,000 g/mole.

IR spectrum ($cm^{-1}$):

| 3500 – 2500: | COOH | 3090: | =C—H |
|---|---|---|---|
| 3000 – 2900: | —C—H | 1740 – 1700: | C=O |
| 1650: | C=C | 980 + 920: | allyl group |

Solubility tests in acetone or toluene showed that the polymer was not cross-linked. The powdery substance was incorporated into a polymerizable resin, bis-GMA/HEMA (2,2-bis-4(2-hydroxy-3-methacryloxy-propyloxy)-phenyl-propane/2-hydroxyethyl-methacrylate). The mixture was allowed to cure. The mechanical properties of the resin matrix were not deteriorated by the polymer. The values remained unchanged even after extended immersion in water of the material.

Example 2

To 20 ml of tetrahydrofuran chilled to −70° to −80° C., there was added 0.5 ml of a 2M solution of n-butyl lithium in cyclohexane (1 mmol). Then, 15 ml (13.35 g/84.5 mmol) of methacrylic acid trimethylsilyl ester were quickly added, the viscosity thereby increasing significantly. After stirring for 30 minutes, 5 ml (4.70 g/37.2 mmol) of allyl methacrylate were added. Stirring was continued for 30 minutes. The reaction was discontinued by adding 2 ml of ethanol. The trimethylsilyl groups were removed by stirring overnight with 5 ml of 10% aqueous HCl solution. The polymer was precipitated, then washed and dried in vacuo.

The molecular weight determined by GPC was 30,000 g/mole.

IR spectrum ($cm^{-1}$):

| 3500 – 2500: | COOH | 3090: | =C—H |
|---|---|---|---|
| 3000 – 2900: | —C—H | 1740 – 1700: | C=O |
| 1650: | C=C | 980 + 920: | allyl group |

1H-NMR spectrum in DMSO-D6 (ppm):

| 12.4 | broad singlet | | —COOH |
|---|---|---|---|
| 5.9 | broad singlet | 1H | allyl group |
| 5.3 | double duplet | 2H | |
| 4.5 | broad singlet | 2H | |
| 0.7–1.9 | multiplet | | $CH_2$ + $CH_3$ (polymer chain) |

Evaluation of the integral ratios revealed a monomers ratio of approx. 1.9:1 (methacrylic acid trimethylsilyl ester-:allyl methacrylate), i. e. incorporation of the methacrylic acid trimethylsilyl ester is not quite satisfactory when comparing the ratio of incorporated monomers with the mole ratio of the starting components (2.3:1). Solubility tests in N-methyl-2-pyrrolidone or ethanol showed that the polymer was not cross-linked.

Based on these results this material is believed to have the following structure:

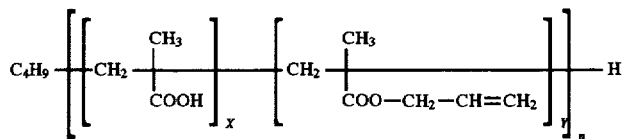

wherein:
x=180–200
y=80–100
n=1

When mixing the powdery substance described hereinabove with glass ionomer powder and a small quantity of water, a pasty glass ionomer cement is obtained which sets within a few minutes to a rubber-like consistency and cures within 30 minutes to a solid and hard material.

I claim:

1. Polymerizable, block-structured oligo- and polyalkenoic acids of the formula

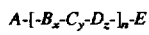

wherein
   a) the groups A and E, being the same or different, are selected from the group consisting of hydrogen, halogen atoms, methacrylate-, acrylate-, allyl-, vinyl-, alkyl-, aryl-, alkoxy-, aryloxy-, carboxyl-, amine-, hydroxy-, isocyanate-, silyl, and siloxy groups,
   b) group B is a segment consisting of sequences selected from the group consisting of mono-, di-, tricarboxylic acids as monomeric units, the anhydrides, salts, and derivatives thereof having an acid protective group on each unit, and where the monomeric unit can be different for each n,
   c) group C is a segment consisting of sequences selected from the group consisting of mono-, di-, tricarboxylic acid esters, and the amides thereof as monomeric units, wherein the alcohol component of the esters and the amine component of the amides each are unsaturated and where the monomeric unit can be different for each n,
   d) group D is a segment consisting of sequences selected from the group consisting of mono-, di-, tricarboxylic adds as monomeric units, their esters, amides, and nitriles not containing any double bonds, and where the monomeric unit can be different for each n,
   e) where the groups B, C, and D within these blocks [-B$_x$-C$_y$-D$_z$-] can be in any order and can be different for each n, and
   f) where the index n represents 1 to 10 and where the indices x, y, and z each range from 0 to 1,000, wherein for at least one n, x is at least 4 and y is at least 4, where x, y, and z can be different for each n.

2. Polymerizable, block-structured oligo- and polyalkenoic acids according to claim 1 characterized in that the groups B, C, and D are segments selected from the group consisting of sequences of acrylic acid, methacrylic acid, maleic acid, itaconic acid, and, respectively, their esters, anhydrides, amides, nitriles and derivatives.

3. Polymerizable, block-structured oligo- and polyalkenoic acids according to claim 1 characterized in that the acid protective groups defined in b) for Group B are selected from the group consisting of trialkylsilyl and -siloxy esters.

4. Polymerizable, block-structured oligo- and polyalkenoic acids according to claim 1 characterized in that the alcohol components of the esters or the amine components of the amides defined in c) for Group C are selected from the group consisting of vinyl, allyl and vinylidene.

5. Polymerizable, block-structured oligo- and polyalkenoic acids according to claim 1 characterized in that the alcohol components of the esters or the amine components of the amides defined in d) for Group D are selected from the group consisting of alkyl, particularly methyl, ethyl, propyl, tert-butyl, substituted aryl, and unsubstituted aryl.

6. Polymerizable, block-structured oligo- and polyalkenoic acids according to claim 1 characterized in that group C is a segment selected from the group consisting of oligomeric/polymeric sequences of methacrylic acid allyl ester and vinyl ester and group B is a segment selected from the group consisting of oligomeric/polymeric sequences of methacrylic acid trimethylsilyl ester and any other derivative of said acid which can be hydrolyzed to yield an acid.

7. Polymerizable, block-structured oligo- and polyalkenoic acids according to claim 1 characterized in that the index n represents 1 to 4.

8. The method of using the polymerizable, block-structured oligo- and polyalkenoic acids of claim 1 for dental and medical purposes, comprising:
   adding at least one of the polymerizable block-structured oligo- and polyalkenoic acids of claim 1 to a composition effective for dental and medical purposes; and
   reacting said block-structured oligo- and polyalkenoic acids.

9. The method of using the polymerizable, block-structured oligo- and polyalkenoic acids of claim 1 comprising:
   adding at least one of the polymerizable block-structured oligo- and polyalkenoic acids as a constituent of molded articles, fissure sealants, adhesion promoters, bonds, surface-modifying preparations, preps and conditioners, and
   reacting said block-structured oligo- and polyalkenoic acids.

10. The method of using the polymerizable, block-structured oligo- and polyalkenoic acids of claim 1 comprising:
    adding at least one of the polymerizable, block-structured oligo- and polyalkenoic acids as a component in polymerizable glass ionomer cements; and
    reacting said block-structured oligo- and polyalkenoic acids.

11. The polymerizable, block-structured oligo- and polyalkenoic acids of claim 1
    g) where the polymerizable, block-structured oligo- and polyalkenoic acids and their precursors, respectively, ate formed by anionic polymerization.

12. Polymerizable, block-structured oligo- and polyalkenoic acids of the formula

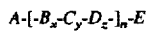

wherein
   a) the groups A and E, being the same or different, are selected from the group consisting of hydrogen, halogen atoms, methacrylate-, acrylate-, allyl-, vinyl-, alkyl-, aryl-, alkoxy-, aryloxy-, carboxyl-, amine-, hydroxy-, isocyanate-, silyl, and siloxy groups,
   b) group B is a segment consisting of sequences selected from the group consisting of mono-, di-, tricarboxylic acids as monomeric units, the anhydrides, salts, and derivatives thereof, having an acid protective group on each unit, and where the monomeric unit can be different for each n,
   c) group C is a segment consisting of sequences selected from the group consisting of mono-, di-, tricarboxylic acid esters, and the amides thereof as monomeric units, wherein the alcohol component of the esters and the amine component of the amides each are unsaturated and where the monomeric unit can be different for each n,
   d) group D is a segment consisting of sequences selected from the group consisting of mono-, di-, tricarboxylic adds as monomeric units, their esters, amides, and nitriles not containing any double bonds, and where the monomeric unit can be different for each n,
   e) where the groups B, C, and D within these blocks [-B$_x$-C$_y$-D$_z$-] can be in any order and can be different for each n, and f) where the index n represents 1 to 10 and where the indices x, y, and z each range from 4 to 1,000, where x, y, and z can be different for each n.

13. Polymerizable, block-structured oligo- and polyalkenoic acids according to claim 12 characterized in that the groups B, C, and D are segments selected from the group consisting of sequences of acrylic acid, methacrylic acid, maleic acid, itaconic acid, and, respectively, their esters, anhydrides, amides, nitriles and derivatives.

14. Polymerizable, block-structured oligo- and polyalkenoic acids according to claim 12 characterized in that the acid protective groups defined in b) for Group B are selected from the group consisting of trialkylsilyl and -siloxy esters.

15. Polymerizable, block-structured oligo- and polyalkenoic acids according to claim 12 characterized in that the alcohol components of the esters or the amine components of the amides defined in c) for Group C are selected from the group consisting of vinyl, allyl and vinylidene.

16. Polymerizable, block-structured oligo- and polyalkenoic acids according to claim 12 characterized in that the alcohol components of the esters or the amine components of the amides defined in d) for Group D are selected from the group consisting of alkyl, particularly methyl, ethyl, propyl, tert-butyl, substituted aryl, and unsubstituted aryl.

17. Polymerizable, block-structured oligo- and polyalkenoic acids according to claim 12 characterized in that the index n represents 1 to 4.

18. The method of using the polymerizable, block-structured oligo- and polyalkenoic acids of claim 12 for dental and medical purposes comprising:
adding at least one of the polymerizable, block-structured oligo- and polyalkenoic acids of claim 11 to a composition effective for dental and medical purposes; and
reacting said block-structured oligo- and polyalkenoic acids.

19. The method of using the polymerizable, block-structured oligo- and polyalkenoic acids of claim 12 comprising:
adding at least one of the polymerizable, block-structured oligo- and polyalkenoic acids as a constituent of molded articles, fissure sealants, adhesion promoters, bonds, surface-modifying preparations, preps and conditioners; and
reacting said block-structured oligo- and polyalkenoic acids.

20. The method of using the polymerizable, block-structured oligo- and polyalkenoic acids of claim 12 comprising:
adding at least one of the polymerizable, block-structured oligo- and polyalkenoic acids as a component in polymerizable glass ionomer cements; and
reacting said block-structured oligo- and polyalkenoic acids.

21. The polymerizable, block-structured oligo- and polyalkenoic acids of claim 12
g) where the polymerizable, block-structured oligo- and polyalkenoic acids and their precursors, respectively, are formed by anionic polymerization.

22. Polymerizable, block-structured oligo- and polyalkenoic acids of the formula $$A\text{-}[\text{-}B_x\text{-}C_y\text{-}D_z\text{-}]_n\text{-}E$$

wherein
a) the groups A and E, being the same or different, are selected from the group consisting of hydrogen, halogen atoms, methacrylate-, acrylate-, allyl-, vinyl-, alkyl-, aryl-, alkoxy-, aryloxy-, carboxyl-, amine-, hydroxy-, isocyanate-, silyl, and siloxy groups,
b) group B is a segment consisting of sequences selected from the group consisting of methacrylic acid trimethylsilyl ester and any other derivative of said acid which can be hydrolyzed to yield an acid, having an acid protective group on each unit, and where the monomeric unit can be different for each n,
c) group C is a segment consisting of sequences selected from the group consisting of methacrylic acid allyl ester and vinyl esters as monomeric units, wherein the alcohol component of the esters are unsaturated and where the monomeric unit can be different for each n,
d) group D is a segment consisting of sequences selected from the group consisting of mono-, di-, tricarboxylic acids as monomeric units, their esters, amides, and nitriles not containing any double bonds, and where the monomeric unit can be different for each n,
e) where the groups B, C, and D within these blocks [-$B_x$-$C_y$-$D_z$-] can be in any order and can be different for each n, and
f) where the index n represents 1 to 10 and where the indices x, y, and z each range from 4 to 1,000, where x, y, and z can be different for each n.

23. The polymerizable, block-structured oligo- and polyalkenoic acids of claim 22
g) where the polymerizable, block-structured oligo- and polyalkenoic acids and their precursors, respectively, are formed by anionic polymerization.

* * * * *

UNITED STATES PATENT AND TRADEMARK OFFICE
CERTIFICATE OF CORRECTION

PATENT NO : 5,753,765
DATED : May 19, 1998
INVENTOR(S) : Sven Arne Thomsen

It is certified that error appears in the above-identified patent and that said Letters Patent is hereby corrected as shown below:

Column 7, line 29, delete the word "adds" and insert therefor the word --acids--.

Column 8, line 35, delete the word "ate" and insert therefor the word --are--.

Column 8, line 62, delete the word "adds" and insert therefor the word --acids--.

Signed and Sealed this

First Day of June, 1999

Attest:

Attesting Officer

Q. TODD DICKINSON

Acting Commissioner of Patents and Trademarks